United States Patent
Chen et al.

(10) Patent No.: US 11,145,217 B2
(45) Date of Patent: Oct. 12, 2021

(54) AUTONOMOUS SPEECH AND LANGUAGE ASSESSMENT

(71) Applicant: FUJITSU LIMITED, Kawasaki (JP)

(72) Inventors: Cong Chen, Cupertino, CA (US); Ajay Chander, San Francisco, CA (US); Kanji Uchino, Santa Clara, CA (US)

(73) Assignee: FUJITSU LIMITED, Kawasaki (JP)

( * ) Notice: Subject to any disclaimer, the term of this patent is extended or adjusted under 35 U.S.C. 154(b) by 738 days.

(21) Appl. No.: 15/711,947

(22) Filed: Sep. 21, 2017

(65) Prior Publication Data

US 2019/0088151 A1    Mar. 21, 2019

(51) Int. Cl.
| | |
|---|---|
| *G09B 5/06* | (2006.01) |
| *G09B 19/04* | (2006.01) |
| *G10L 13/02* | (2013.01) |
| *G10L 15/22* | (2006.01) |
| *G06F 40/143* | (2020.01) |
| *G06F 8/34* | (2018.01) |
| *G06F 9/451* | (2018.01) |

(52) U.S. Cl.
CPC ............ *G09B 5/06* (2013.01); *G06F 40/143* (2020.01); *G09B 19/04* (2013.01); *G10L 13/02* (2013.01); *G10L 15/22* (2013.01); *G06F 8/34* (2013.01); *G06F 9/451* (2018.02)

(58) Field of Classification Search
CPC ....................................................... G09B 5/06
USPC ........................................................ 434/185
See application file for complete search history.

(56) References Cited

U.S. PATENT DOCUMENTS

| | | | |
|---|---|---|---|
| 2006/0074689 A1* | 4/2006 | Cosatto | G06T 13/40 704/275 |
| 2015/0195406 A1* | 7/2015 | Dwyer | H04M 3/42221 379/265.07 |

OTHER PUBLICATIONS

Rosenbaum, Sara, and Patti Simon, eds. Speech and Language Disorders in Children: Implications for the Social Security Administration's Supplemental Security Income Program. National Academies Press, (2016).
NIH, Quick Statistics About Voice, Speech, Language. https://www.nidcd.nih.gov/health/statistics/quick-statistics-voice-speech-language, (2016).
Santen, Jan PH, Richard W. Sproat, and Alison Presmanes Hill. "Quantifying repetitive speech in autism spectrum disorders and language impairment." Autism Research 6.5 (2013): 372-383.
Losh, Molly, and Peter C. Gordon. "Quantifying narrative ability in autism spectrum disorder: A computational linguistic analysis of narrative coherence." Journal of autism and developmental disorders 44.12 (2014): 3016-3025.

(Continued)

*Primary Examiner* — Kesha Frisby
(74) *Attorney, Agent, or Firm* — Maschoff Brennan

(57) ABSTRACT

Technologies are described to provide autonomous speech and language assessments. In some examples, a method to conduct an autonomous speech and language assessment includes facilitating authoring of an autonomous speech and language assessment. The autonomous speech and language assessment may be interactions between one or more of a conversational module, an analytical module, and a control module, and the interaction may be specified using a visual programming language. The method may also include modeling the autonomous speech and language assessment as a graph using a conversation markup language, and conducting the autonomous speech and language assessment utilizing a conversational virtual agent.

19 Claims, 8 Drawing Sheets

(56) References Cited

OTHER PUBLICATIONS

Kory, Jacqueline, and Cynthia Breazeal. "Storytelling with robots: Learning companions for preschool children's language development." The 23rd IEEE International Symposium on Robot and Human Interactive Communication. IEEE, (2014).

Gordon, Goren, et al. "Affective Personalization of a Social Robot Tutor for Children's Second Language Skills." Thirtieth AAAI Conference on Artificial Intelligence. (2016).

* cited by examiner

```xml
<?xml version="1.0" encoding="UTF-8"?>
<conversationml xmlns="http://graphml.graphdrawing.org/xmlns"
    xmlns:xsi="http://www.w3.org/2001/XMLSchema-instance"
    xsi:schemaLocation="http://graphml.graphdrawing.org/xmlns
    http://graphml.graphdrawing.org/xmlns/1.0/graphml.xsd">
<graph id="A conversation" edgedefault="directed">
<node id="n1" name = "Children01" ModuleID = "ImageView" APIURL = "http://localhost/imageview" APIParameters = "image=children.png;duration=20" />
<node id="n2" name = "Touch his shoes" ModuleID = "AudioPlayer" APIURL = "http://localhost/audioplayer" APIParameters = "audiofile=touchhisshoes.wav;repeat=2"/>
<node id="n3" name = "Detect touching his shoes" ModuleID = "TouchInput" APIURL = "http://localhost/touchinput" APIParameters = "sourcemodule=ImageView"/>
<node id="n4" name = "TouchedShoes" ModuleID = "EqualTo" APIURL = "http://localhost/equalto" APIParameters = "HisShoes"/>
<node id="n5" name = "Correct" ModuleID = "AudioPlayer" APIURL = "http://localhost/audioplayer" APIParameters = "Goodjob.wav"/>
<node id="n6" name = "Check attempts" ModuleID = "LessThan" APIURL = "http://localhost/lessthan" APIParameters = "2" />
<node id="n7" name = "Try again" ModuleID = "AudioPlayer" APIURL = "http://localhost/audioplayer" APIParameters = "Tryagain.wav"/>
<node id="n8" name = "Score" ModuleID = "Score" APIURL = "http://localhost/score" APIParameters = "item=01"/>
<edge id = "e1" source="n1" target="n2"/>
<edge id = "e2" source="n2" target="n3"/>
<edge id = "e3" source="n3" target="n4"/>
<edge id = "e4" source="n4" target="n5" passingvalue = "true"/>
<edge id = "e5" source="n4" target="n6" passingvalue = "false"/>
<edge id = "e6" source="n5" target="n8"/>
<edge id = "e7" source="n6" target="n8" passingvalue = "false"/>
<edge id = "e8" source="n6" target="n7" passingvalue = "true"/>
<edge id = "e9" source="n7" target="n3"/>
</graph>
</conversationml>
```

*FIG. 6*

AUTONOMOUS SPEECH AND LANGUAGE ASSESSMENT

FIELD

The described technology relates generally to speech and language assessments.

BACKGROUND

Presently, large percentage of children in the U.S. may be afflicted with speech and language disorders. Research has determined that these disorders in young children can negatively affect subsequent educational achievement, e.g., reading, writing, social, etc. Articulation and phonology disorders are a common form of such speech and language disorders.

Childhood apraxia of speech (CAS) is a motor speech disorder in which a child with CAS has difficulty saying sounds, syllables, and words correctly. Aphasia is the inability a person to comprehend and formulate language due to damage to specific regions of the person's brain. Stuttering (also known as stammering) is a speech disorder in which the flow of speech is disrupted by involuntary repetitions and prolongations of sounds, syllables, words or phrases. Selective Mutism is a childhood anxiety disorder characterized by a child's inability to speak and communicate effectively in select social settings.

Speech and language assessments are typically administered or conducted manually via conversation, observation, and questionnaire. There are numerous standardized speech and language assessments for different types of speech and language disorders. For example, Preschool Language Scales—Fifth Edition (PLS-5) is designed for use with children aged 0-7 to assess language development and identify language disorders. During a PLS-5 assessment, a human examiner (e.g., a speech-language pathologist or clinician) may ask an individual who is being tested (e.g., a child) to perform a battery of tasks, such as performing an action in response to a verbal instruction given by the examiner (e.g., for testing auditory comprehension), or answering a question regarding a picture shown by the examiner (e.g., for testing expressive communication ability). Based on the individual's responses, the speech-language pathologist may then be able to diagnose the individual's speech disorder and its severity.

Automated assessment techniques, such as computational linguistics and natural language programming (NLP), may be used to automatically assess the individual's responses to, for example, assist in the diagnosis. Unfortunately, the conversations with the individual being tested still need to be administered manually by the human examiner.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

According to some examples, a speech and language assessment system may include conversational modules, each configured to provide a modality of communication. The system may also include an analysis module configured to provide an assessment-specific function. The system may further include a control module configured to provide conditional flow between some of the conversational modules or between some of the conversational modules and the analytical module. The system may further include an autonomous speech and language assessment that specifies interactions between at least some of the conversational modules and the analytical module.

The objects and advantages of the embodiments will be realized and achieved at least by the elements, features, and combinations particularly pointed out in the claims. Both the foregoing general description and the following detailed description are given as examples, are explanatory and are not restrictive of the invention, as claimed.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 6 illustrates an example conversation markup language snippet that models the example conversation diagram of FIG. 4;

DESCRIPTION OF EMBODIMENTS

Figure 1:
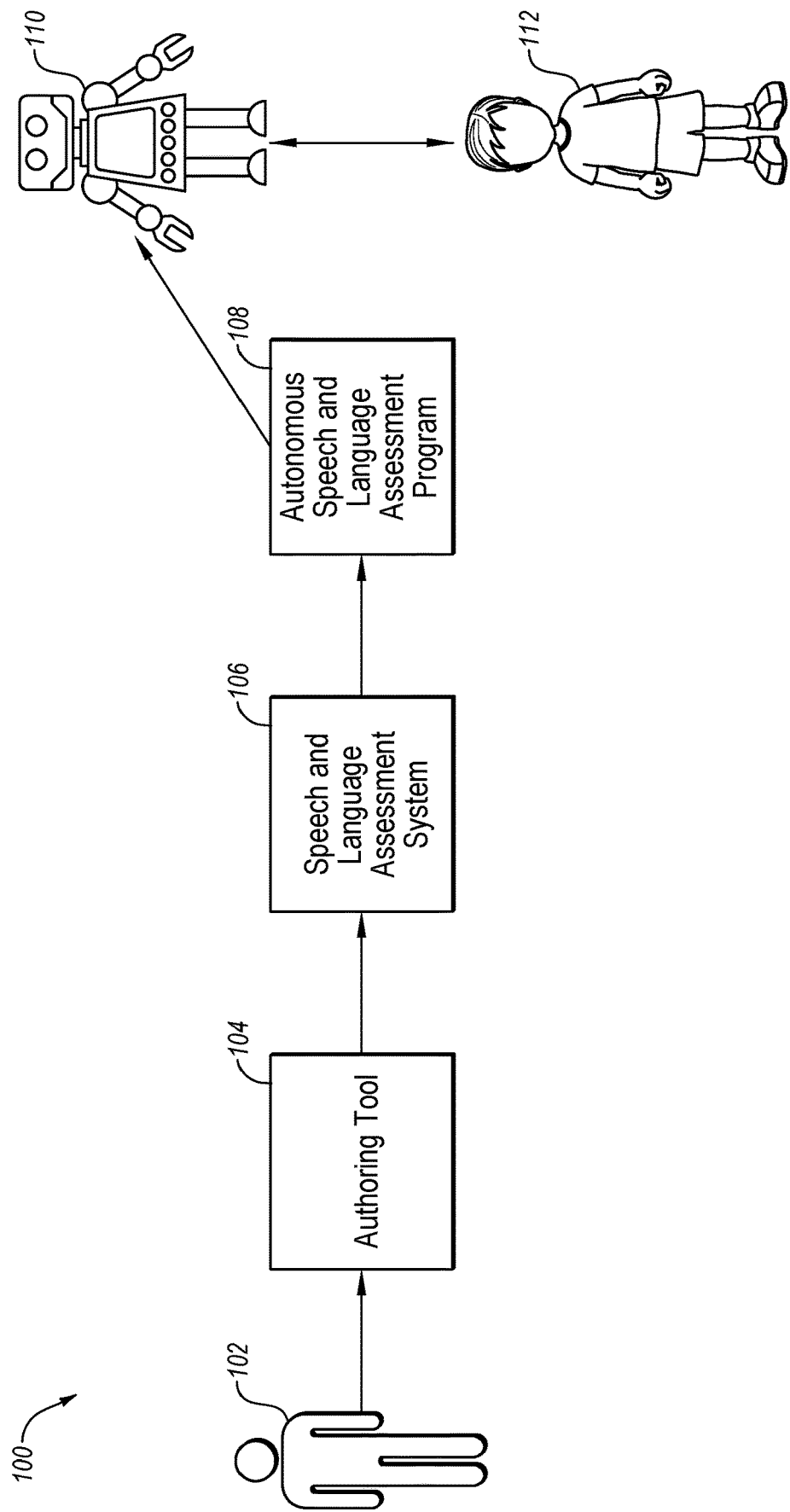
FIG. 1 is a high-level diagram illustrating an example framework in which an autonomous speech and language assessment may be conducted.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to technologies including methods, apparatus, systems, devices, and/or computer program products related to authoring and autonomously administering speech and language assessments using a conversational virtual agent.

Technologies are generally described for a speech and language assessment system and an authoring tool (an e-learning speech and analysis creation tool) that facilitates the creation of autonomous speech and language assessments (e.g., autonomous speech and language assessment programs). The authoring tool may provide a user interface, such as a graphical user interface (GUI), for use in creating autonomous speech and language assessments. The autonomous speech and language assessments may include customized content (e.g., conversations, conversational content, tests, etc.) to be delivered to an individual being tested, and the assessments (e.g., analysis) that are to be performed as part of the autonomous speech and language assessments to diagnose or evaluate the individual for specific speech and language disorders. The speech and language assessment system and/or the autonomous speech and language assessments may be executed on, or by, a conversational virtual agent. Examples of conversational virtual agents may include, without limitation, robots, computers, computing devices, mobile computing devices, computing systems, etc.

The speech and language assessment system may include one or more conversational modules, one or more analytical modules, and one or more control modules. The included conversational modules, analytical modules, and control modules provide the building blocks that allow for the creation of autonomous speech and language assessments. For example, a user, using the user interface provided by the authoring tool, can specify the interactions between one or more conversational modules, one or more analytical modules, or one or more control module to create (author) an autonomous speech and language assessment. In some embodiments, the authoring tool may provide or support a visual programming language that facilitates the creation of programs by manipulating program elements graphically, for example, to create a conversation diagram. Continuing the example above, the user may use the user interface to create or draw a conversation diagram to specify the interactions between the various conversational and analytical modules and, thus, author an autonomous speech and language assessment. In some embodiments, conversational diagrams may be modeled using a conversation markup language (CML).

The conversational modules may provide the various types or modalities of communication that are supported by the speech and language assessment system. The provided types of communication are made available for use in authoring the autonomous speech and language assessments. The conversational modules may provide for the manner in which the autonomous speech and language assessments and, more particularly, the customized content may be delivered. Examples of the types of communication may include, with limitation, text, image, audio, text-to-speech, video, touch input, speech recognition, etc. The control module may provide for various types of decisions (conditional flow) to direct the flow or interaction between modules included in the autonomous speech and language assessment system (for example, the flow or interaction between the conversational modules or between the conversational modules and the analytical modules, etc.).

The analytical modules may provide assessment-specific functions or processes. The assessment-specific functions and/or processes may be used to create the assessments to be performed as part of the autonomous speech and language assessment (e.g., to analyze the results of the delivery of the customized content). Examples of assessment-specific functions and processes may include, without limitation, tokenizer (e.g., to divide text into a sequence of tokens (similar to words), etc.), vocabulary analyzer (e.g., to count the number of words and phrases (in different lengths), the complexity of words, etc.), pronunciation analyzer (e.g., to measure articulation, prosody, etc.), syntax analyzer (e.g., to check grammatical correctness, complexity, etc.), fluency analyzer (e.g., to check for continuity, speed, etc.), scoring (e.g., to score the results, etc.), reporting (e.g., to report the results in standard format, etc.), etc. For example, such functions and processes may be implemented by utilizing conventional computational linguistics or natural language programming (NLP).

In some embodiments, the analytical modules may be third-party and/or off-the-shelf programs or components that allow for the creation of the assessments to be performed in the autonomous speech and language assessments. Alternatively or additionally, the analytical modules may provide functionalities for creating assessments without the use of (that is, assessment not based on) such third-party and/or off-the-shelf programs or components. For example, one or more analytical modules may provide a programming interface that allows for the creating of analytical programs that may be incorporated into the autonomous speech and language assessments.

In some embodiments, the speech and language assessment system may optionally include one or more extension modules. The extension modules may provide functionalities to integrate third-party and/or off-the-shelf components into the autonomous speech and language assessments. Examples of third-party and/or off-the-shelf components may include readily-available conversational agents and analytical components that provide application programming interfaces (APIs) to interact with (e.g., access the functionality of) such components. The extension modules may provide compatible APIs to integrate one or more third-party and/or off-the-shelf components.

As discussed above, a user may use the speech and language assessment system to create autonomous speech and language assessments. That is, the user may use the authoring tool to specify the interactions between the various conversational modules, analytical modules, and/or control modules included in the speech and language assessment system to create the autonomous speech and language assessments. The user may also incorporate functionalities provided by components integrated into the speech and language assessment system via the extension modules. For example, a user interested in testing for apraxia of speech in children via audio can create or draw a conversation diagram that specifies specific interactions between the various conversational, control, and analytical modules to define a flow between the modules to test a child for apraxia of speech via audio, and the analysis of the child's responses to determine whether the child has apraxia of speech. Similarly, a user interested in testing people for aphasia via text can create or draw a conversation diagram that specifies specific interactions between the various conversational, control, and analytical modules to define a flow between the modules to test an individual for aphasia via text, and the analysis of the individual's responses to determine whether the individual has aphasia. Among other possible benefits, the speech and language assessment system provides for the dynamic authoring and the autonomous administering of speech and language assessments using a conversational virtual agent.

Turning now to the figures, FIG. 1 is a high-level diagram illustrating an example framework 100 in which an autonomous speech and language assessment may be conducted, arranged in accordance with at least some embodiments described herein. The illustrated framework is only one example of a suitable operating framework and is not intended to suggest any limitation as to the scope of use or functionality of the autonomous speech and language assessment. As illustrated, framework 100 includes an examiner 102, an authoring tool 104, a speech and language assessment system 106, an autonomous speech and language assessment program 108, a conversational virtual agent 110, and an assessment target 112.

Framework 100 facilitates the authoring and autonomous administering of speech and language assessments. Examiner 102 may be a person, such as an assessment administrator, who is interested in creating autonomous speech and language assessments. Authoring tool 104 may be configured to provide access to speech and language assessment system 106. In some embodiments, authoring tool 104 may include a graphical user interface (GUI) with which to access speech and language assessment system 106. The GUI may provide graphical elements for use in creating the autonomous speech and language assessments. Speech and language assessment system 106, which is further described below, may be configured to facilitate the creation or authoring of autonomous speech and language assessments (e.g., autonomous speech and language assessment program 108). Autonomous speech and language assessment program 108 may include modules provided by speech and language assessment system 106, and the connections or flow between the modules. The modules represent the customized content (e.g., conversational content) and assessments that are to be performed as part of the autonomous speech and language assessments, and the connections represent the flow or control between the modules. Conversational virtual agent 110 may be any suitable computing device or system suitable to execute autonomous speech and language assessment program 108. As depicted in FIG. 1, conversational virtual agent 110 is depicted as a robot. Assessment target 112 may be any person, such as a child, etc., that may be the recipient of the autonomous speech and language assessment.

Accordingly, by way of an example, framework 100 may allow examiner 102 to use speech and language assessment system 106, for example, using the authoring tool 104, to author autonomous speech and language assessment program 108 that tests for a specific speech or language disorder. Examiner 102 may then use conversational virtual agent 110 to execute autonomous speech and language assessment program 108 to test assessment target 112 for the speech or language condition or disorder.

In some embodiments, authoring tool 104, speech and language assessment system 106, and conversational virtual agent 110 may be provided in a distributed manner across different computing devices or systems. For example, authoring tool 104 may be executed as a client application on a first computing device, such as a personal computer, and speech and language assessment system 106 may be executed on a second computing device, such as a server computing system. In some embodiments, authoring tool 104 and speech and language assessment system 106 may be provided on the same computing device or system. For example, authoring tool 104 and speech and language assessment system 106 may be executed on conversational virtual agent 110 or a computing device or system other than conversational virtual agent 110.

Figure 2:
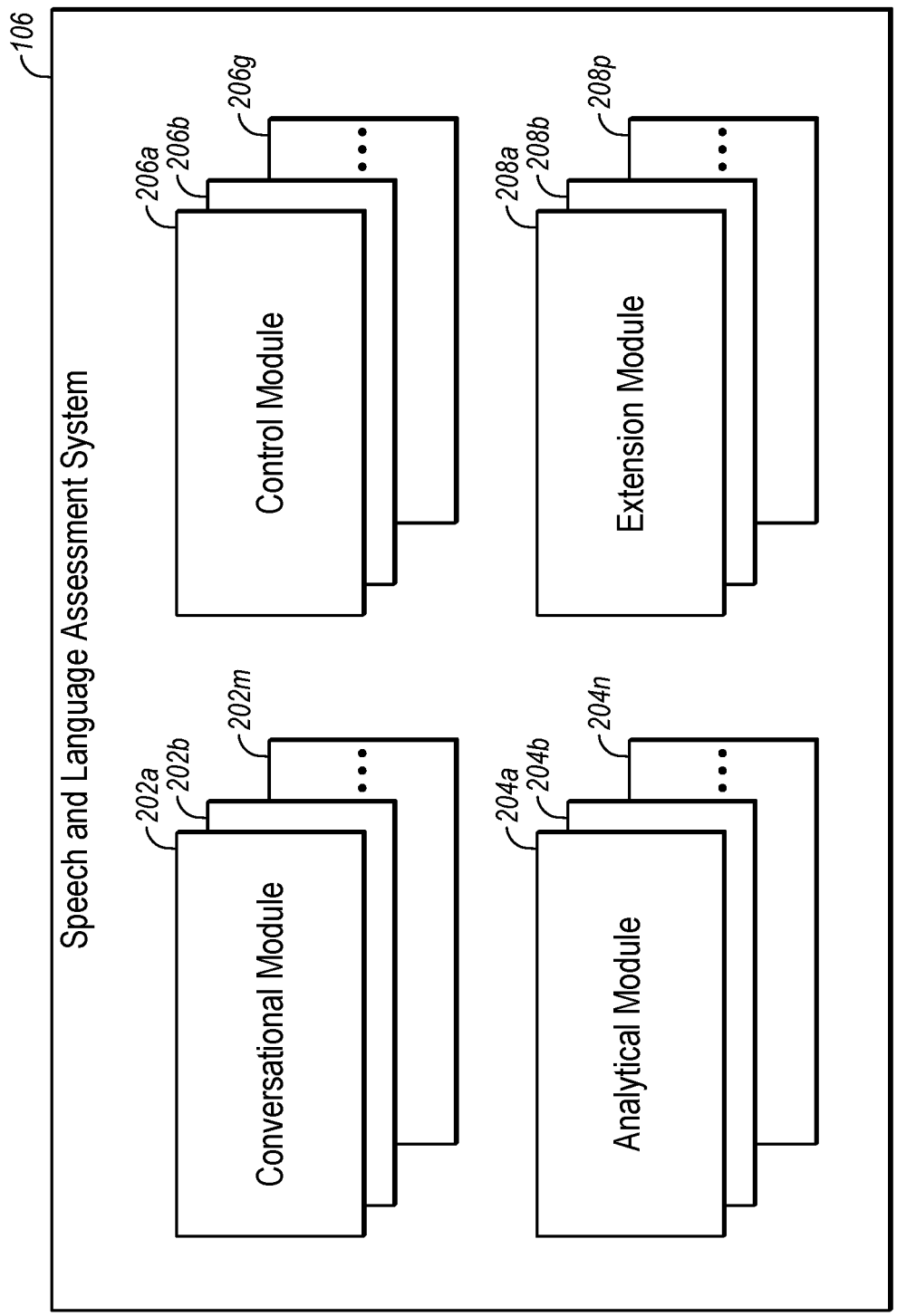
FIG. 2 illustrates selected components of an example speech and language assessment system.

FIG. 2 illustrates selected components of example speech and language assessment system 106, arranged in accordance with at least some embodiments described herein.

Speech and language assessment system 106 may include one or more conversational modules 202a, 202b, . . . , 202m (collectively referred to as conversational modules 202), one or more analytical modules 204a, 204b, . . . , 204n (collectively referred to as analytical modules 204), one or more control modules 206, 206b, . . . , 206g (collectively referred to as control modules 206) and, optionally, one or more extension modules 208a, 208b, . . . , 208p (collectively referred to as extension modules 208). The number of modules depicted in speech and language assessment system 106 is for illustration, and one skilled in the art will appreciate that there may be a different number of conversational modules 202, analytical modules 204, control modules 206, and optional extension modules 208. The modules included in speech and language assessment system 106 provide the building blocks for the conversations used in the assessments (e.g., autonomous speech and language assessment program 108).

Conversational modules 202 may be configured to provide the types or modalities of communication available to a user of speech and language assessment system 106. Conversational modules 202 may be represented as graphical elements on a GUI provided by authoring tool 104. A user can thus select (e.g., drag-and-drop) graphical elements representing conversational modules 202 to include the types of communication represented by the selected graphical elements in an autonomous speech and language assessment.

Analytical modules 204 may be configured to provide the assessment-specific functions or processes available to a user of speech and language assessment system 106. Similar to conversational modules 202, analytical modules 204 may be represented as graphical elements on a GUI provided by authoring tool 104. A user can thus select (e.g., drag-and-drop) graphical elements representing analytical modules 204 to include the assessment-specific processing represented by the selected graphical elements in an autonomous speech and language assessment.

Control modules 206 may be configured to provide decisional or conditional flow between modules (e.g., conversational modules and analytical modules). The types of decisional or conditional flow are available to a user of speech and language assessment system 106 in authoring the autonomous speech and language assessments. Similar to conversational modules 202 and analytical modules 204, the types of decisional or conditional flow may be represented as graphical elements on a GUI provided by authoring tool 104. A user can thus select (e.g., drag-and-drop) graphical elements to specify the flow or control between the modules included in an autonomous speech and language assessment.

Extension modules 208 may optionally be included in speech and language assessment system 106. Extension modules 208 may be configured to provide interfaces, such as APIs, to integrate one or more third-party and/or off-the-shelf components. When included, extension modules 208 provide for the integration of third-party and/or off-the-shelf components into speech and language assessment system 106. These components may provide integration of conventional functionality or processing such as, by way of example, tokenizer, vocabulary analyzer, pronunciation analyzer, etc.

Figure 3:
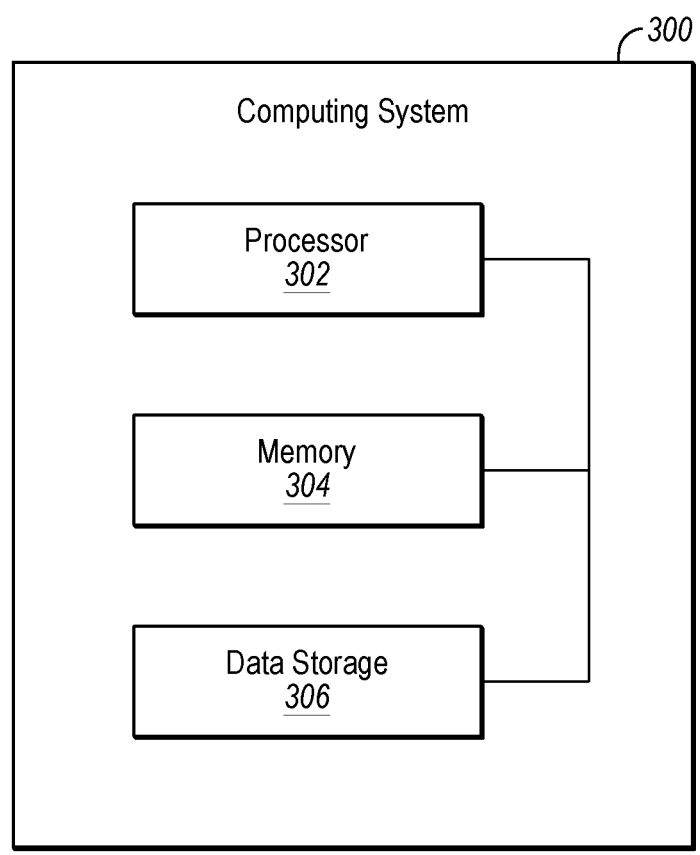
FIG. 3 illustrates selected components of an example general purpose computing system, which may be used to provide autonomous speech and language assessments.

FIG. 3 illustrates selected components of an example general purpose computing system 300, which may be used to provide autonomous speech and language assessments, arranged in accordance with at least some embodiments described herein. Computing system 300 may be configured to implement or direct one or more operations associated with an authoring tool (e.g., authoring tool 104 of FIG. 1), a speech and language assessment system (e.g., speech and language assessment system 106 of FIG. 1), and an autonomous speech and language assessment program (e.g., autonomous speech and language assessment program 108 of FIG. 1). Computing system 300 may include a processor 302, a memory 304, and a data storage 306. Processor 302, memory 304, and data storage 306 may be communicatively coupled.

In general, processor 302 may include any suitable special-purpose or general-purpose computer, computing entity, or computing or processing device including various computer hardware, firmware, or software modules, and may be configured to execute instructions, such as program instructions, stored on any applicable computer-readable storage media. For example, processor 302 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data. Although illustrated as a single processor in FIG. 3, processor 302 may include any number of processors and/or processor cores configured to, individually or collectively, perform or direct performance of any number of operations described in the present disclosure. Additionally, one or more of the processors may be present on one or more different electronic devices, such as different servers.

In some embodiments, processor 302 may be configured to interpret and/or execute program instructions and/or process data stored in memory 304, data storage 306, or memory 304 and data storage 306. In some embodiments, processor 302 may fetch program instructions from data storage 306 and load the program instructions in memory 304. After the program instructions are loaded into memory 304, processor 302 may execute the program instructions.

For example, in some embodiments, any one or more of the authoring tool, the speech and language assessment system, and the autonomous speech and language assessment program may be included in data storage 306 as program instructions. Processor 302 may fetch some or all of the program instructions from the data storage 306 and may load the fetched program instructions in memory 304. Subsequent to loading the program instructions into memory 304, processor 302 may execute the program instructions such that the computing system may implement the operations as directed by the instructions.

Memory 304 and data storage 306 may include computer-readable storage media for carrying or having computer-executable instructions or data structures stored thereon. Such computer-readable storage media may include any available media that may be accessed by a general-purpose or special-purpose computer, such as processor 302. By way of example, and not limitation, such computer-readable storage media may include tangible or non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause processor 302 to perform a certain operation or group of operations.

Modifications, additions, or omissions may be made to computing system 300 without departing from the scope of the present disclosure. For example, in some embodiments, computing system 300 may include any number of other components that may not be explicitly illustrated or described herein.

Figure 4:
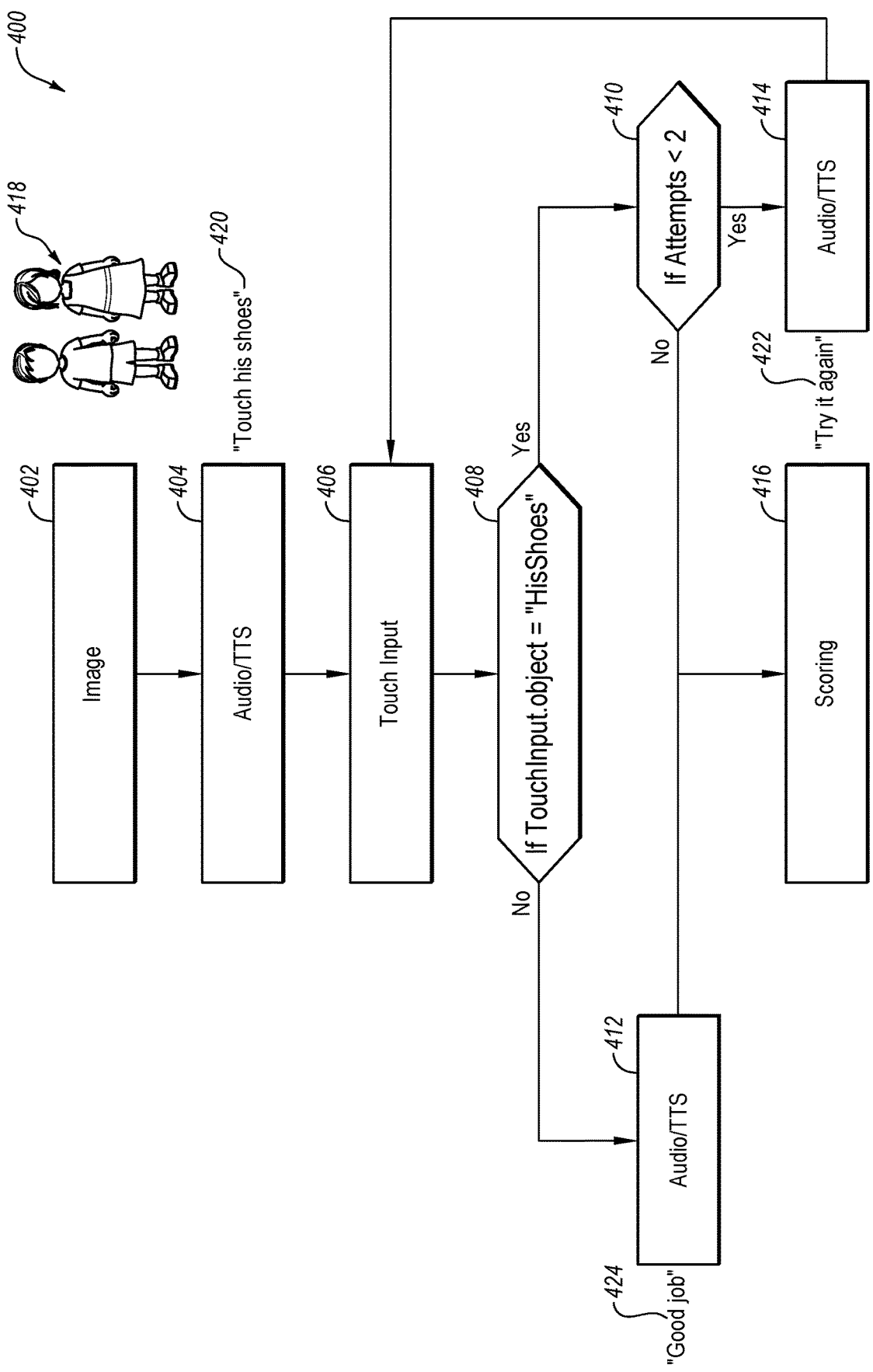
FIG. 4 illustrates an example conversation diagram of a task in an example autonomous speech and language assessment.

FIG. 4 illustrates an example conversation diagram 400 of a task in an example autonomous speech and language assessment, arranged in accordance with at least some embodiments described herein. For example, conversation diagram 400 is what examiner 102 may create and see when authoring the autonomous speech and language assessment. As illustrated, conversation diagram 400 is a flow diagram that defines the flow of the autonomous speech and language assessment. In conversation diagram 400, blocks 402, 404, 406, 412, and 414 represent conversational modules, block 416 represents an analytical module, and decision blocks 408 and 410 represent control modules. Decision blocks 408 and 410 represent decisions that direct the autonomous speech and language assessment flow to different destinations depending on a condition. The connections between the blocks and decision blocks represent the speech and language assessment flow. Blocks 402, 404, 406, 408, 410, 412, and 414 may represent the customized content component, and block 416 may represent the assessment component of the illustrated autonomous speech and language assessment.

As illustrated by conversation diagram 400, the autonomous speech and language assessment is to start by displaying an image 418 (block 402), for example, to a child being autonomously tested. The autonomous speech and language assessment is to then audibly generate "Touch his shoes" 420 (block 404), and then wait for a response or an action (block 406). The autonomous speech and language assessment then determines whether the detected response was a touching of the shoes (i.e., whether the child being tested touched the boy's shoes in image 418) (decision block 408). If the detected response was a touching of the boy's shoes, the autonomous speech and language assessment is to audibly generate "Good job" 424 (block 412), and then score (analyze) the detected response (block 416). Otherwise, if the detected response was not a touching of the boy's shoes (e.g., the girl's shoes instead, an indication of inability to understand gender-specific pronouns), the autonomous speech and language assessment is to determine whether the child had two attempts to touch his shoes (decision block 410). If the child already had two attempts, the autonomous speech and language assessment is to score (analyze) the already detected two responses (block 416). Otherwise, if the child did not have two attempts to touch his shoes, the autonomous speech and language assessment is to audibly generate "Try it again" 422 (block 414), and then wait for another response or an action (block 406). The final score of the entire assessment (including multiple of such tasks) may be an indication of whether the child has a speech or language disorder.

Figure 5:
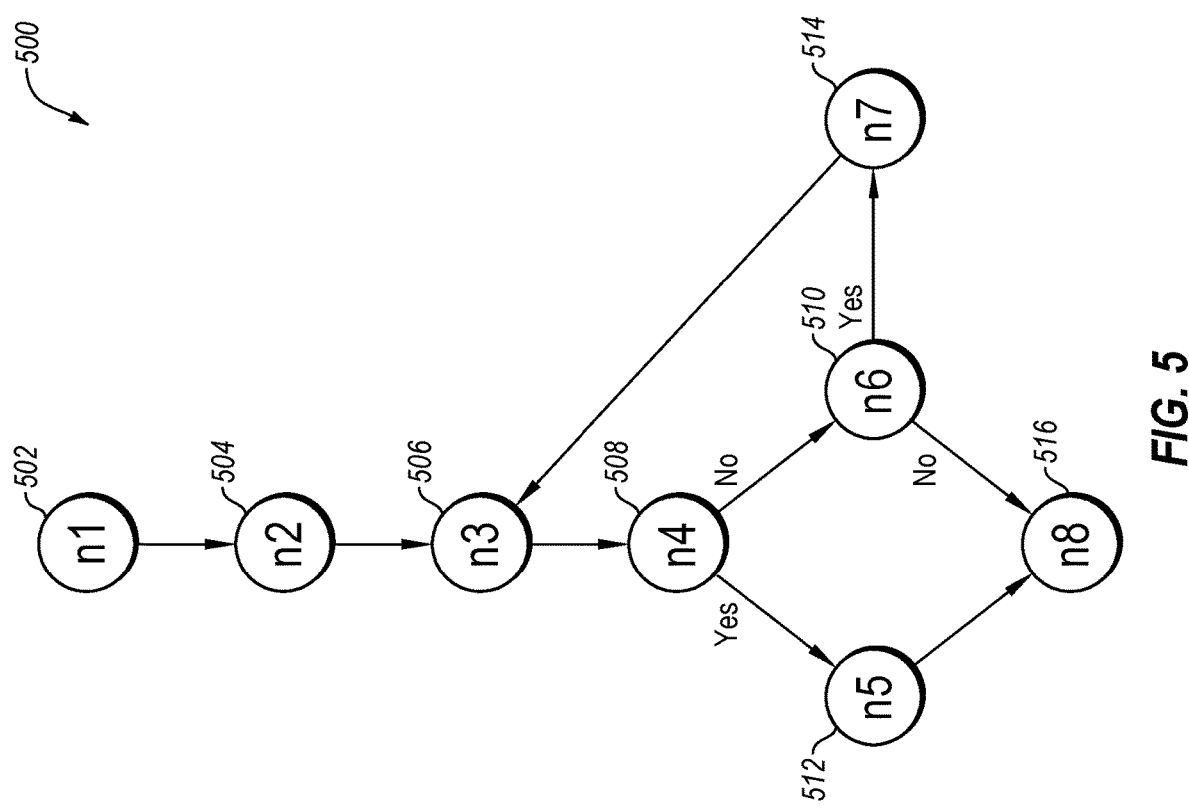
FIG. 5 illustrates an example conversation graph that corresponds to the example conversation diagram of FIG. 4.

FIG. 5 illustrates an example conversation graph 500 that corresponds to example conversation diagram 400 of FIG. 4, arranged in accordance with at least some embodiments described herein. Speech and language assessment system 106 may model conversation diagram 400 as conversation graph 500, for example, using a conversation markup language (CML). In general, a conversation graph includes nodes and edges that represent a conversation. A node represents a function or control (e.g., a conversational module, an analytical module, or a control module), and an edge represents a connection of the function or control. The edges are directed in that conversational flow goes from one end to the other.

As illustrated in conversation graph 500, nodes 502, 504, 506, 512, and 514 represent conversational modules, node 516 represents an analytical module, and nodes 508 and 510 represent control modules. Nodes 502, 504, 506, 508, 510, 512, 514, and 516 of conversation graph 500 correspond to blocks 402, 404, 406, 408, 410, 412, 414, and 416 of conversation diagram 400, respectively. That is, there is a one-to-one correlation between the nodes in conversation graph 500 and the blocks in conversation diagram 400. The edges in conversation graph 500 represent connections between the nodes, and are directed to correspond to the flow in corresponding conversation diagram 400.

FIG. 6 illustrates an example conversation markup language (CML) snippet 600 that models example conversation diagram 400 of FIG. 4, arranged in accordance with at least some embodiments described herein. For example, speech and language assessment system 106 may use CIVIL snippet 600 to model conversation diagram 400 as conversation graph 500. CML may be similar to graph markup language (GML) in that a CML file may represent a conversation by specifying graph attributes, node attribute, and edge attributes. A graph attribute includes a unique identifier for the graph (graph id) and an indication of the default edge type (edgedefault). The ID identifies the graph being represented by the CML file, and the edge type is directed by default. A node attribute includes a unique identifier for the node (node id), a description of the node (name), a unique identifier of the module (ModuleID), an specification of a Uniform Resource Locator (URL) of the module (APIURL), and specification of any parameters as defined by the module, separated by semicolons (APIParameters). The specified URL may be local or remote. An edge attribute includes a unique identifier for the edge (edge id), the identifier of the source node (source), the identifier of the destination node (target), and a specification of a condition to pass this edge (passingvalue). The edge is passed when the output from the source node meets the condition specified by passingvalue.

More particularly, selected attributes of CML snippet 600 are illustrated in FIG. 6. As illustrated, a graph attribute 602 identifies the graph as a conversation (graph id="A conversation") whose edges are directed (edgedefault="directed"). A node attribute 604 indicates that the identified node (node id="n1") represents a display of an image (ModuleID="ImageView"). Node attribute 604 also indicates the location of the image to display (the URL specified by APIURL), and specifies that the image is to be displayed for 20 seconds (APIParameters=" . . . ; duration=20"). A node attribute 606 indicates that the identified node (node id="n2") represents a playing of an audio file (ModuleID="AudioPlayer"). Node attribute 606 also indicates the location of the audio file to play (the URL specified by APIURL), and specifies that the playing of the audio file may be repeated two times (APIParameters=" . . . ; repeat=2"). An edge attribute 608 indicates that the identified edge (edge id="e8") connects nodes n6 and n7 (source="n6" target="n7"). Edge attribute 608 also specifies that the conversation flow passes this edge when the output of n6 is true (passingvalue="true"). Node attributes 602 and 604 correspond to nodes 502 and 504, respectively, and edge attribute 608 corresponds to the edge between node 510 and node 514 of conversation graph 500.

Figure 7:
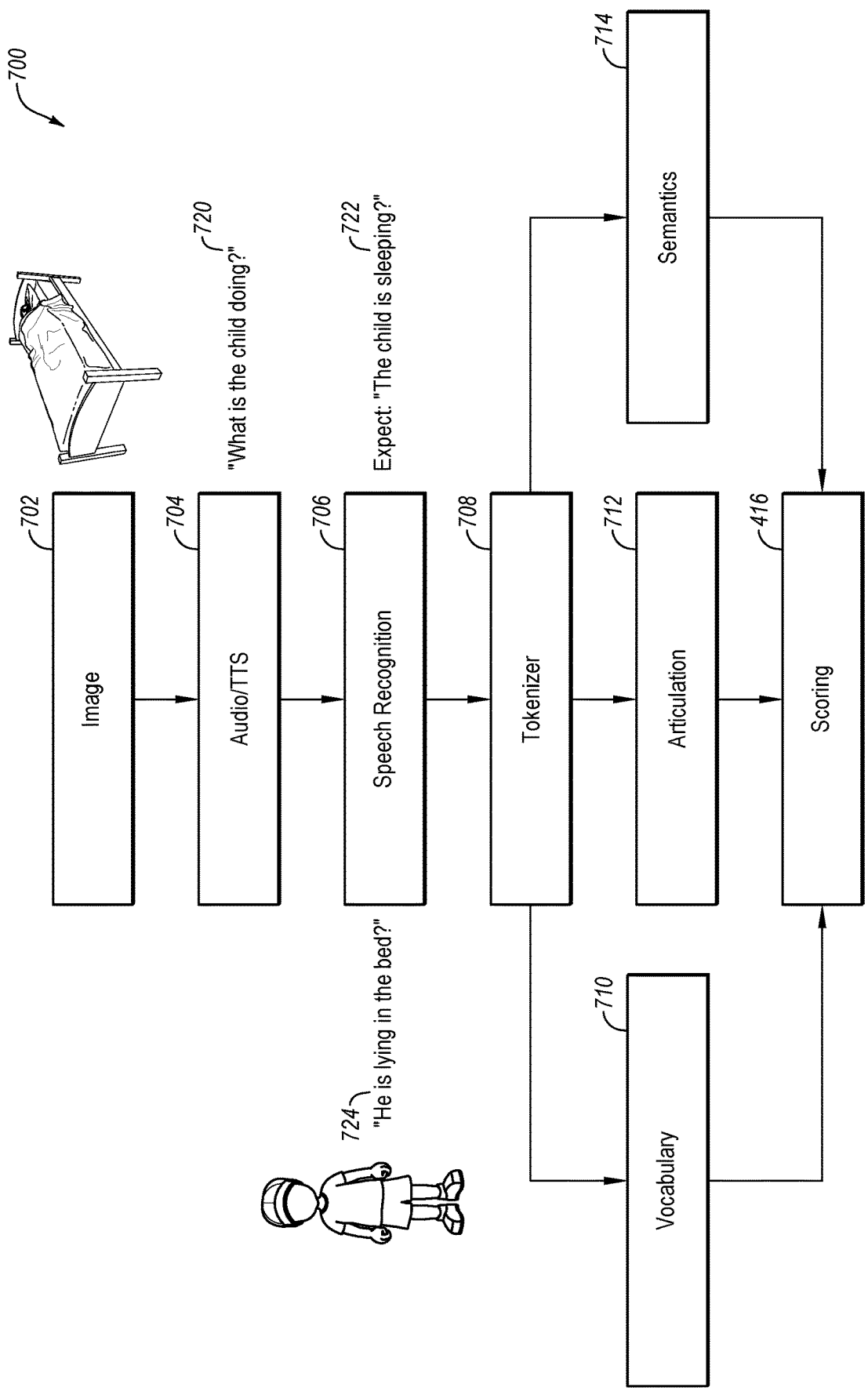
FIG. 7 illustrates a task in an example conversation diagram of another example autonomous speech and language assessment.

FIG. 7 illustrates an example conversation diagram 700 of another example autonomous speech and language assessment, arranged in accordance with at least some embodiments described herein. As illustrated, conversation diagram 700 is a flow diagram that defines the flow of the autonomous speech and language assessment. In conversation diagram 700, blocks 702, 704, and 706 represent conversational modules, and blocks 708, 710, 712, 714, and 716 represent control modules. Conversation diagram 700 does not include any decision modules. The connections between the blocks represent the speech and language assessment flow. Blocks 702, 704, and 706 may represent the customized content component, and blocks 708, 710, 712, 714, and 716 may represent the assessment component of the illustrated autonomous speech and language assessment.

As illustrated by conversation diagram 700, the autonomous speech and language assessment is to start by displaying an image 718 (block 702), for example, to an individual being autonomously tested. The autonomous speech and language assessment is to then audibly ask the question "What is the child doing?" 720 (block 704), and then wait for an audible response (block 706). The autonomous speech and language assessment expects the response to be "The child is sleeping" 722, but receives "He is lying in the bed" 724 as the audible response. The autonomous speech and language assessment then analyzes the received response to compare the received response to the expected response. The analysis may involve tokenizing the response (block 708), and processing the tokens to determine vocabulary (block 710), articulation (block 712), and comparing semantics of the received and expected responses (block 714). The autonomous speech and language assessment then scores the received response (e.g., scores the results of the analysis) (block 716).

Figure 8:
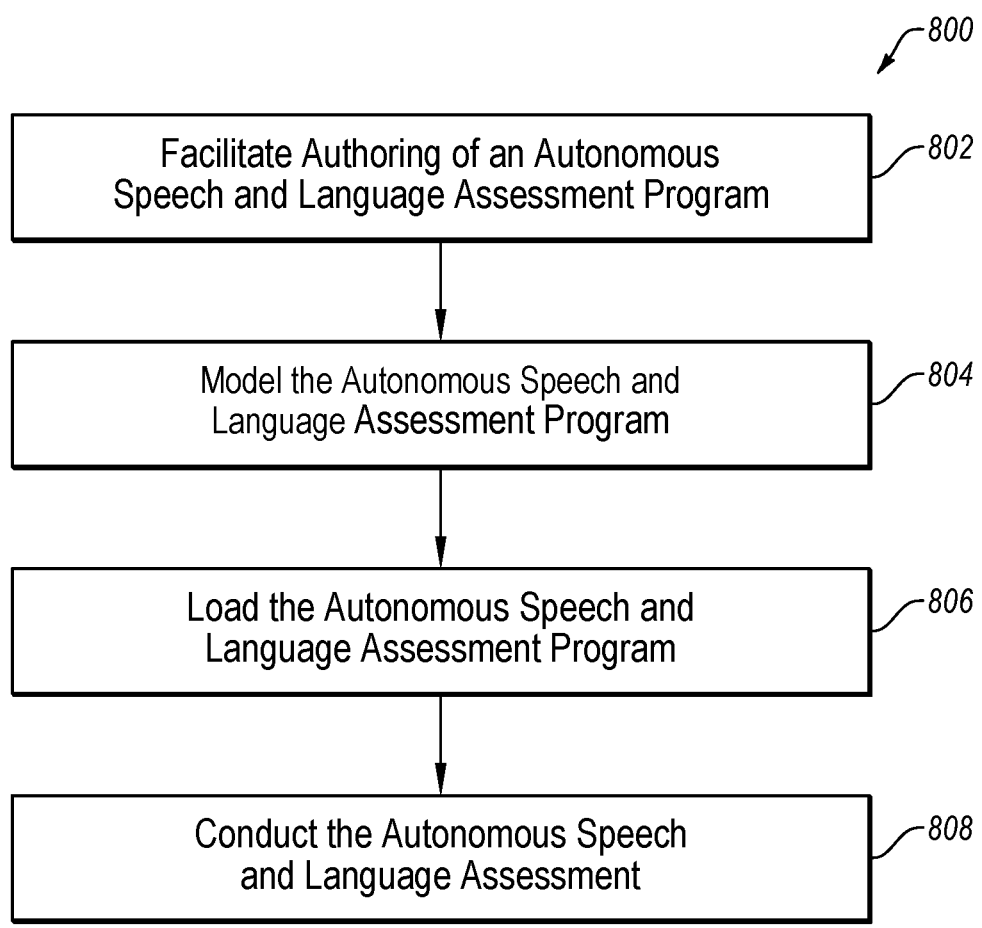
FIG. 8 is a flow diagram that illustrates an example process to provide an autonomous speech and language assessment that may be performed by a computing system such as the computing system of FIG. 3, all arranged in accordance with at least some embodiments described herein.

FIG. 8 is a flow diagram 800 that illustrates an example process to provide an autonomous speech and language assessment that may be performed by a computing system such as computing system 300 of FIG. 3, arranged in accordance with at least some embodiments described herein. Example processes and methods may include one or more operations, functions or actions as illustrated by one or more of blocks 802, 804, 806, and/or 808, and may in some embodiments be performed by a computing system such as computing system 300 of FIG. 3. The operations described in blocks 802-808 may also be stored as computer-executable instructions in a computer-readable medium such as memory 304 and/or data storage 306 of computing system 300.

As depicted by flow diagram 800, the example process to provide autonomous speech and language assessment may begin with block 802 ("Facilitate Authoring of an Autonomous Speech and Language Assessment Program"), where speech and language assessment system 106 may provide access to authoring tool 104 for use by a user to author an autonomous speech and language assessment program. For example, the user may use authoring tool 104 to generate a conversation diagram to create an autonomous speech and language assessment program that tests individuals for speech disorders.

Block 802 may be followed by block 804 ("Model the Autonomous Speech and Language Assessment Program"), where speech and language assessment system 106 may model the generated autonomous speech and language assessment program as a conversation graph. Speech and language assessment system 106 may generate a CML program to model the generated conversation diagram that represents the generated autonomous speech and language assessment program as a conversation graph. In some embodiments, authoring tool 104 may be configured to model the generated conversation diagram as a conversation graph.

Block 804 may be followed by block 804 ("Load the Autonomous Speech and Language Assessment Program"), where the autonomous speech and language assessment program is loaded for autonomous execution. For example, the user may load the autonomous speech and language assessment program (e.g., the CML program that models the autonomous speech and language assessment program) on a conversational virtual agent.

Block 806 may be followed by block 808 ("Conduct the Autonomous Speech and Language Assessment"), where the loaded autonomous speech and language assessment program is executed to autonomously conduct the speech and language assessment. For example, the conversation virtual agent on which the CML program is loaded may execute the CML program to autonomously conduct the speech and language assessment.

As indicated above, the embodiments described in the present disclosure may include the use of a special purpose or general purpose computer (e.g., the processor 302 of FIG. 3) including various computer hardware or software modules, as discussed in greater detail herein. Further, as indicated above, embodiments described in the present disclosure may be implemented using computer-readable media (e.g., the memory 304 of FIG. 3) for carrying or having computer-executable instructions or data structures stored thereon.

As used in the present disclosure, the terms "module" or "component" may refer to specific hardware implementations configured to perform the actions of the module or component and/or software objects or software routines that may be stored on and/or executed by general purpose hardware (e.g., computer-readable media, processing devices, etc.) of the computing system. In some embodiments, the different components, modules, engines, and services described in the present disclosure may be implemented as objects or processes that execute on the computing system (e.g., as separate threads). While some of the system and methods described in the present disclosure are generally described as being implemented in software (stored on and/or executed by general purpose hardware), specific hardware implementations, firmware implements, or any combination thereof are also possible and contemplated. In this description, a "computing entity" may be any computing system as previously described in the present disclosure, or any module or combination of modulates executing on a computing system.

Terms used in the present disclosure and in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

All examples and conditional language recited in the present disclosure are intended for pedagogical objects to aid the reader in understanding the present disclosure and the concepts contributed by the inventor to furthering the art, and are to be construed as being without limitation to such specifically recited examples and conditions. Although embodiments of the present disclosure have been described in detail, various changes, substitutions, and alterations could be made hereto without departing from the spirit and scope of the present disclosure.

What is claimed is:

1. A speech and language assessment system, comprising:
    a plurality of conversational modules, each conversational module configured to provide a modality of communication;
    an analytical module configured to provide an assessment-specific function;
    a control module configured to provide conditional flow between some of the plurality of conversational modules or between some of the plurality of conversational modules and the analytical module; and
    an autonomous speech and language assessment, the autonomous speech and language assessment specifies interactions between at least some of the plurality of conversational modules and the analytical module, wherein the autonomous speech and language assessment is executable by a conversational virtual agent which engages in a virtual conversation with a user, the user being assessed for speech and language disorders.

2. The system of claim 1, wherein the autonomous speech and language assessment further specifies an interaction with the control module.

3. The system of claim 1, further comprising an authoring tool configured to provide a graphical user interface suited to create the autonomous speech and language assessment.

4. The system of claim 3, wherein the interaction between the at least some conversational modules and the analytical module is specified as a conversation diagram, the conversation diagram being created using the graphical user interface.

5. The system of claim 1, further comprising an extension module configured to provide integration of a third-party component.

6. The system of claim 1, wherein the autonomous speech and language assessment includes a customized content and an assessment.

7. The system of claim 6, wherein the assessment is conducted utilizing the assessment-specific function provided by the analytical module.

8. The system of claim 6, wherein the customized content is delivered utilizing the modality of communication provided by the at least one of the plurality of conversational modules.

9. A method to conduct an autonomous speech and language assessment, the method comprising:
  facilitating authoring of an autonomous speech and language assessment, the autonomous speech and language assessment being interactions between one or more of a conversational module, an analytical module, and a control module, the interaction being specified using a visual programming language;
  modeling the autonomous speech and language assessment as a graph using a conversation markup language; and
  conducting the autonomous speech and language assessment utilizing a conversational virtual agent which engages in a virtual conversation with a user, the user being assessed for speech and language disorders.

10. The method of claim 9, wherein conducting the autonomous speech and language assessment includes one or more of text communication, image communication, audio communication, video communication, touch input, text-to-speech, or speech recognition.

11. The method of claim 9, wherein authoring of the autonomous speech and language assessment is through a graphical user interface.

12. The method of claim 9, wherein the autonomous speech and language assessment is a standardized test.

13. The method of claim 9, wherein the autonomous speech and language assessment includes a customized content and an assessment.

14. The method of claim 13, wherein the customized content is conversational content.

15. The method of claim 14, wherein conducting the autonomous speech and language assessment utilizing the conversational virtual agent includes delivery of the conversational content by the conversational virtual agent.

16. A non-transitory computer-readable storage media storing thereon instructions that, in response to execution by a processor, causes the processor to:
  facilitate authoring of an autonomous speech and language assessment, the autonomous speech and language assessment including a customized content and an assessment, the autonomous speech and language assessment being created as a conversation diagram;
  model the autonomous speech and language assessment as a graph based on a conversation markup language; and
  load the autonomous speech and language assessment on a conversational virtual agent, wherein the autonomous speech and language assessment is executable by a conversational virtual agent which engages in a virtual conversation with a user, the user being assessed for speech and language disorders.

17. The non-transitory computer-readable storage media of claim 16, further storing thereon instructions that, in response to execution by the processor, causes the processor to provide an authoring tool to facilitate authoring of the autonomous speech and language assessment.

18. The non-transitory computer-readable storage media of claim 16, wherein the autonomous speech and language assessment is a standardized test.

19. The non-transitory computer-readable storage media of claim 16, wherein the customized content is conversational content.

* * * * *